United States Patent
Baek et al.

(10) Patent No.: US 11,564,793 B2
(45) Date of Patent: Jan. 31, 2023

(54) NOSE IMPLANT MANUFACTURING METHOD

(71) Applicants: ANYMEDI INC., Seoul (KR); Jung Hwan Baek, Seoul (KR)

(72) Inventors: Jung Hwan Baek, Seoul (KR); Guk Bae Kim, Seoul (KR); Seung Hyun Choi, Hanam-si (KR); Yun Jung Choi, Gyeongju-si (KR); Do Yun Lee, Seoul (KR)

(73) Assignees: ANYMEDI INC., Seoul (KR); Jung Hwan Baek, Seoul (KR)

( * ) Notice: Subject to any disclaimer, the term of this patent is extended or adjusted under 35 U.S.C. 154(b) by 0 days.

(21) Appl. No.: 17/056,320

(22) PCT Filed: Aug. 31, 2018

(86) PCT No.: PCT/KR2018/010143
§ 371 (c)(1),
(2) Date: Nov. 17, 2020

(87) PCT Pub. No.: WO2019/221338
PCT Pub. Date: Nov. 21, 2019

(65) Prior Publication Data
US 2021/0251745 A1    Aug. 19, 2021

(30) Foreign Application Priority Data
May 17, 2018  (KR) .................. 10-2018-0056637

(51) Int. Cl.
*G16H 30/20*        (2018.01)
*A61F 2/18*         (2006.01)
(Continued)

(52) U.S. Cl.
CPC .......... *A61F 2/186* (2013.01); *G05B 19/4097* (2013.01); *G16H 30/20* (2018.01);
(Continued)

(58) Field of Classification Search
CPC ........ A61B 2034/102; A61B 2034/105; A61B 2034/108; A61B 34/10; A61B 6/032;
(Continued)

(56) References Cited

U.S. PATENT DOCUMENTS 5,133,754 A  *  7/1992  Laghi ................. B29C 45/1676
                                                  623/8
2008/0215149 A1*  9/2008  Bae ........................... A61F 2/12
                                                  623/11.11
(Continued)

FOREIGN PATENT DOCUMENTS

KR    10-2006-0111375 A      10/2006
KR       2006-0111375 A   *  10/2006
(Continued)

OTHER PUBLICATIONS

Supplementary European Search Report dated Jul. 21, 2021 in European Application No. 18919230.5.
(Continued)

*Primary Examiner* — Kidest Bahta
(74) *Attorney, Agent, or Firm* — Bridgeway IP Law Group, PLLC; Hyun Woo Shin

(57) ABSTRACT

The present disclosure relates to a method for manufacturing nose implant, including obtaining a 3-dimensional image of a nasal bone and a 3-dimensional image of a nasal cavity; modeling a nasal cartilage by applying information of anatomy between the nasal bone, nasal cavity, and nasal cartilage, to the 3-dimensional image of the nasal bone and the 3-dimensional image of the nasal cavity; and modeling an inner shape of where the implant may be seated, from the 3-dimensional image of the nasal bone and the modelled nasal cartilage.

12 Claims, 21 Drawing Sheets

(51) Int. Cl.
*G05B 19/4097* (2006.01)
*A61B 6/03* (2006.01)

(52) U.S. Cl.
CPC ......... *A61B 6/032* (2013.01); *A61F 2240/002* (2013.01); *G05B 2219/35134* (2013.01)

(58) Field of Classification Search
CPC .... A61F 2002/2885; A61F 2002/30948; A61F 2002/30957; A61F 2002/30985; A61F 2240/002; A61F 2/0059; A61F 2/186; A61F 2/2875; A61F 2/30942; G05B 19/4097; G05B 2219/35134; G16H 30/20
See application file for complete search history.

(56) References Cited

U.S. PATENT DOCUMENTS

2015/0198943 A1* 7/2015 Kotlus .................. G06T 19/20
700/98

2017/0360578 A1* 12/2017 Shin ..................... G09B 23/286

FOREIGN PATENT DOCUMENTS

| KR | 10-2015-0087788 A | | 7/2015 |
|---|---|---|---|
| KR | 10-2015-0124052 A | | 11/2015 |
| KR | 10-2016-0001316 A | | 1/2016 |
| KR | 10-2016-0024894 A | | 3/2016 |
| KR | 10-1656088 B1 | | 9/2016 |
| KR | 10-2017-0096344 A | | 8/2017 |
| KR | 10-2017-0096345 A | | 8/2017 |
| KR | 2017-0096344 A | * | 9/2017 |
| WO | 2007/092841 A2 | | 8/2007 |

OTHER PUBLICATIONS

International Search Report in International Application No. PCT/KR2018/010143, filed Aug. 31, 2018.

* cited by examiner (a) SKIN (b) BONE

(c) NASAL CAVITY

IDENTICAL TO ACTUAL ANATOMICAL STRUCTURE

IDENTICAL TO ACTUAL ANATOMICAL STRUCTURE

NOSE IMPLANT MANUFACTURING METHOD

CROSS-REFERENCE TO RELATED APPLICATIONS

This application is the U.S. national stage application of International Patent Application No. PCT/KR2018/010143, filed Aug. 31, 2018, which claims the benefit under 35 U.S.C. § 119 of Korean Application No. 10-2018-0056637, filed May 17, 2018, the disclosures of each of which are incorporated herein by reference in their entirety.

1. FIELD

The present disclosure relates to a method for manufacturing nose implant, and more particularly, to a method for manufacturing a nose implant that may be used in a rhinoplasty surgery.

2. BACKGROUND

Along with the recent increase in interest in beauty, interest in plastic surgery is also exploding. Among facial plastic surgeries, nasal plastic surgeries have been widely performed from the past. And for these nasal plastic surgeries, rhinoplasty is most generally used, which is a technique to raise the appearance of the nose by inserting an artificial implant such as silicone, inside the nose.

In a conventional nasal plastic surgery, the manufacturing method would proceed as the operator selects an implant that conforms to the shape of the patient's nose from implant sets having various lengths and thicknesses, and during the operation, checks the curves of the nose bone and cartilage and then carves the inner shape on which the implant will be seated.

However, this method had a problem that it takes a lot of time and that it is not easy to manufacture an implant of a desired shape by hand carving. Further, if the implant is not placed in close contact with the nasal bone and cartilage, but forms a space in between, side effects such as infection and positional deformation may occur.

SUMMARY

Therefore, a purpose of the present disclosure is to resolve the problems of prior art, that is, to provide a manufacturing method for nose implant, that includes modelling the shape of cartilage that is not identifiable from CT images by applying anatomy information to 3-dimensional images of the nasal bone and nasal cavity, that have been segmented from the CT images, and then modelling a patient-customized inner shape of an implant to be seated by reflecting the shape of the modelled cartilage, thereby reducing the operation time, and providing the implant that may be closely attached to the nasal bone and cartilage and thus does not cause side effects such as infection, positional deformation and the like.

The tasks that the present disclosure intends to resolve are not limited to the aforementioned, and other tasks not mentioned above will also be apparent for those skilled in the art based on the disclosure hereinbelow.

These tasks may be achieved by a method for manufacturing nose implant including (a) obtaining a 3-dimensional image of a nasal bone and a 3-dimensional image of a nasal cavity; (b) modeling a nasal cartilage by applying information of anatomy between the nasal bone, the nasal cavity and the nasal cartilage, to the 3-dimensional image of the nasal bone and the 3-dimensional image of the nasal cavity; and (c) modeling an inner shape of where the implant may be seated, from the 3-dimensional image of the nasal bone and the modelled nasal cartilage.

Here, the step (a) may include obtaining a CT image; and segmenting the 3-dimensional image of the nasal bone and the 3-dimensional image of the nasal cavity from the CT image.

Here, the step (b) may include repeating applying an offset to the 3-dimensional image of the nasal cavity and expanding the image by a constant ratio; and comparing the expanded 3-dimensional image of the nasal cavity and the 3-dimensional image of the nasal bone, and comparing whether the expanded nasal cavity is identical to a height of the nasal bone; and obtaining a 3-dimensional image of the expanded nasal cavity where a first offset has been applied, the first offset being the constant ratio enabling the expanded nasal cavity to be identical to the height of the nasal bone.

Here, the method for manufacturing nose implant may further include, before the step (b), copying a left nasal cavity and a right nasal cavity to be symmetrical based on the nasal cavity that is anatomically close to normal, of the left nasal cavity and the right nasal cavity, in the 3-dimensional image of the nasal cavity.

Here, the method for manufacturing nose implant may further include obtaining the 3-dimensional image of the nasal cavity, that has been expanded by the constant ratio, by applying a second offset, that is obtained by subtracting a value corresponding to a thickness of the nasal cartilage from the first offset, in the 3-dimensional image of the nasal cavity; creating an outline of a lower lateral cartilage or Alar cartilage and upper lateral cartilage on a surface of the 3-dimensional image of the nasal cavity, that has been expanded by applying the second offset; and modeling a 3-dimensional shape of the lower lateral cartilage or Alar cartilage and the upper lateral cartilage by applying a thickness of the nasal cartilage to the outline.

Here, the method for manufacturing nose implant may further include, after the obtaining of the 3-dimensional image of the nasal cavity, that has been expanded by the constant ratio, by applying the second offset, correcting the shape of the nasal cavity according to anatomical structure in the 3-dimensional image of the nasal cavity, that has been expanded by applying the second offset.

Here, the method for manufacturing nose implant may further include modeling both sides of a septal nasal cartilage by applying a third offset from the 3-dimensional image of the nasal cavity; and modeling a the ridge line of the septal nasal cartilage according to a line connecting a location of an end point of the modelled upper lateral cartilage and an end point of a septal nasal bone, to model a 3-dimensional shape of the septal nasal cartilage.

Here, the step (c) may include creating an inner shape line of the implant by connecting a bone line in the 3-dimensional image of the nasal bone and a line of the modelled nasal cartilage; expanding the image where the bone line and the nasal cartilage line are connected by the constant ratio, by applying a fourth offset, that corresponds to a thickness of a mucous membrane; and modelling the inner shape of the implant from the image expanded by the constant ratio by applying the fourth offset.

Here, the method for manufacturing nose implant may further include modeling an entirety of the implant including modeling an outer shape of the implant; modelling a mold for manufacturing a shape of the modelled implant; manufacturing the mold; and manufacturing the nasal implant by injecting silicone into the mold.

Here, the modelling of the outer shape of the implant may include, regarding each cross-section vertical to a nasal longitudinal direction of the implant, obtaining a height between the inner shape and the outer shape of the implant from a difference of height of the ridge of the nose point between skin before plastic surgery and skin after plastic surgery; and free-curve modelling between the ridge of the nose point of the implant and an inner shape edge of the implant, according to shape of the skin after plastic surgery.

Here, the manufacturing of the mold may manufacture the mold using a 3D printer.

According to the method for manufacturing nasal implant of the present disclosure as described above, there is an advantage of being able to manufacture a patient-customized nasal implant using a 3-dimensional imaging technology.

Further, there is an advantage of minimizing the gap between the nasal cartilage and the implant, and thus closely attaching the nasal cartilage and the implant, thereby minimizing the side effects such as inflammation, position deformation and the like.

Further, there is an advantage that the person performing the surgery does not have to carve the implant during the surgery, thereby reducing the surgery time.

Further, there is an advantage that since the nasal implant is manufactured based on the 3-dimensional image, result of the patient's surgery can be predicted more accurately.

DETAILED DESCRIPTION

Figure 1A:
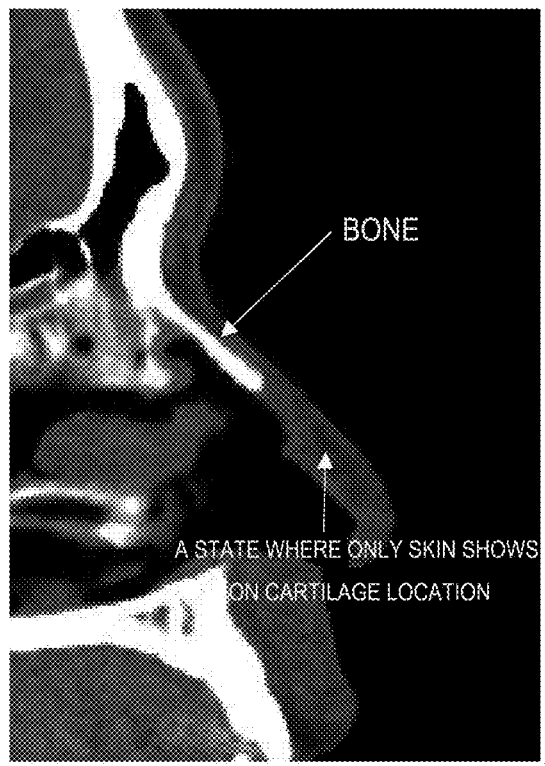
FIGS. 1(a) and 1(b) illustrate CT images taken from the side of the face and from below the chin.

Specific matters of the embodiments are included in the detailed description and the drawings.

Advantages and features of the present disclosure, and the methods for achieving those advantages and features will become apparent with reference to the embodiments described hereinafter in detail together with the drawings attached. However, the present disclosure is not limited by the embodiments disclosed hereinafter, but may be embodied in various different forms. That is, the present embodiments are provided to complete the disclosure of the present invention, and to fully inform the scope of the present disclosure to those of ordinary skill in the art to which the present disclosure pertains, and the present disclosure will be defined by the scope of the claims. Like reference numerals indicate like components throughout the specification.

Hereinbelow, the present disclosure will be described with reference to the drawings for describing the manufacturing method of nose implant according to the embodiments of the present disclosure.

A manufacturing method of nose implant according to an embodiment of the present disclosure may be configured to include obtaining a 3-dimensional image of a nasal bone and a 3-dimensional image of a nasal cavity, modelling a nasal cartilage using the 3-dimensional image of the nasal bone and the 3-dimensional image of the nasal cavity, and modelling an inner shape of where an implant may be seated, based on the 3-dimensional image of the nasal nose and the modelled nasal cartilage. Further, the manufacturing method of nose implant may further include modelling an entirety of the implant including an outer form of the implant, modelling a mold for manufacturing a shape of the modelled implant, manufacturing the mold, and manufacturing a nasal implant by injecting silicone to the mold.

Figure 1B:
Figure 2A:
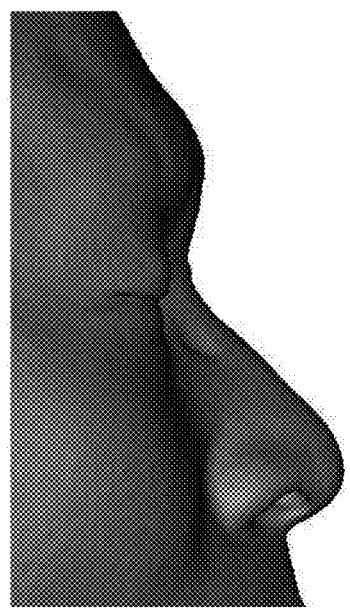
FIGS. 2(a)-2(c) illustrate 3-dimensional images of the skin, bone, and nasal cavity that have been segmented from the CT images of FIGS. 1(a) and 1(b).
Figure 2B:
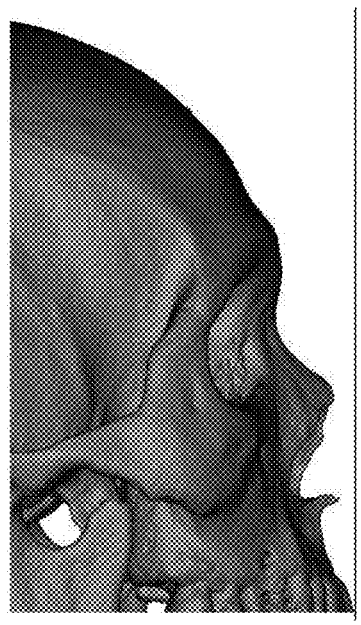
Figure 2C:
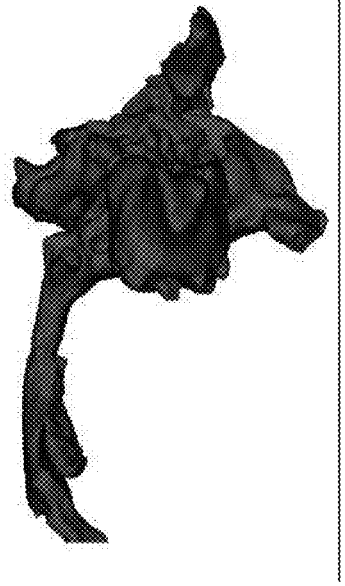

FIGS. 1(a) and 1(b) illustrate CT images taken from the side of the face and from below the chin, and FIGS. 2(a)-2(c) illustrate 3-dimensional images of the skin, bone, and nasal cavity, that have been segmented from the CT images of FIGS. 1(a) and 1(b).

FIG. 1(a) illustrates a CT image taken from the side of the face, and FIG. 1(b) illustrates a CT image taken from below the chin. Generally, it is possible to identify bones, empty spaces inside the body, and skin from the CT images, but not cartilage. For reference, here, it should be noted that bone does not refer to cartilage but hard bone that is identifiable from a CT image. Thus, as shown below, the present disclosure will model the shape of a nasal cartilage that is not identifiable from a CT image, by applying information of anatomy to images identifiable from the CT image, and model the inner shape of a nasal implant, which is a surface where the nasal implant may be seated, based on the modelled nasal cartilage.

First, a 3-dimensional image of a nasal bone and a 3-dimensional image of a nasal cavity are obtained. Moreover, in order to model an outer shape of the nasal implant, a 3-dimensional image of skin may be obtained as well. Here, By segmenting the CT image with adjusting a Housefield Unit (HU) value in the CT image, a 3-dimensional skin image surrounding the nose (FIG. 2(a)), a 3-dimensional nasal bone image (FIG. 2(b)), and a 3-dimensional nasal cavity image (FIG. 2(c)) may be obtained as illustrated in FIGS. 2(a)-2(c). Obtaining images by adjusting the HU value is a well-known technology, and thus detailed description will be omitted.

Next, by applying anatomic information to the 3-dimensional image of the nasal bone and the 3-dimensional image of the nasal cavity, a nasal cartilage is modelled. The process for modeling the nasal cartilage will be described hereinbelow with reference to FIGS. 3(a) to 8.

Figure 3A:
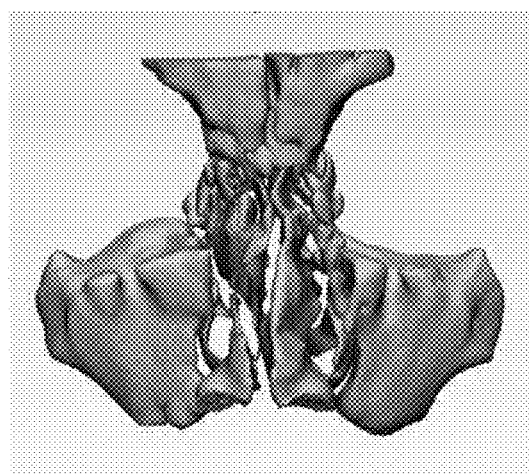
FIGS. 3(a)-3(d) illustrate a part of a process for modelling a lower lateral cartilage and a upper lateral cartilage according to an embodiment of the present disclosure.
Figure 3B:
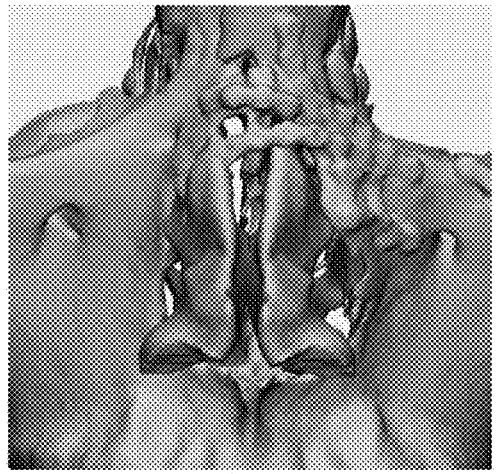
Figure 3C:
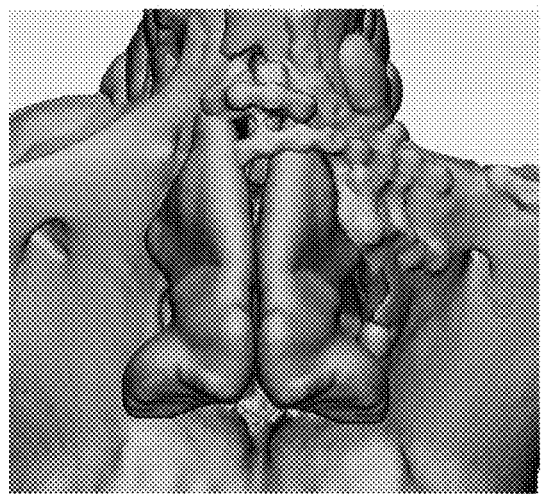
Figure 3D:
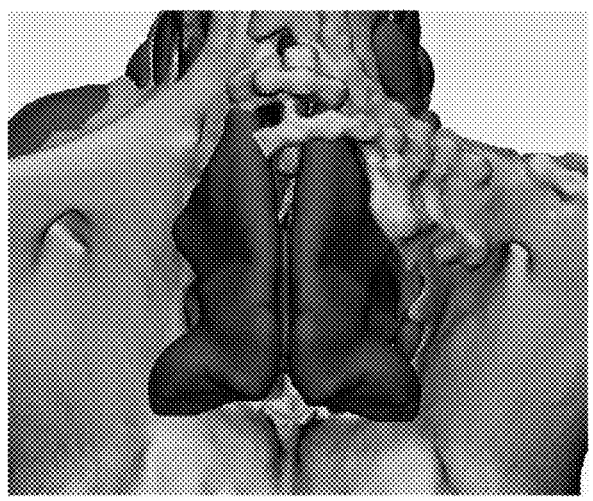
Figure 5A:
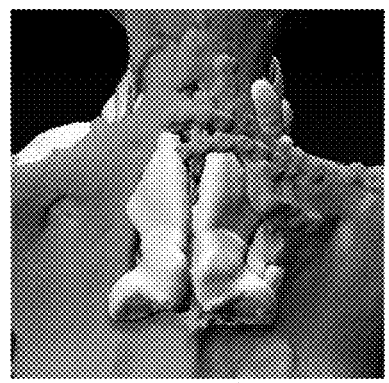
FIGS. 5(a)-5(c) illustrate a part of the process for modelling the lower lateral cartilage and the upper lateral cartilage, following FIGS. 3(a)-3(d).
Figure 5B:
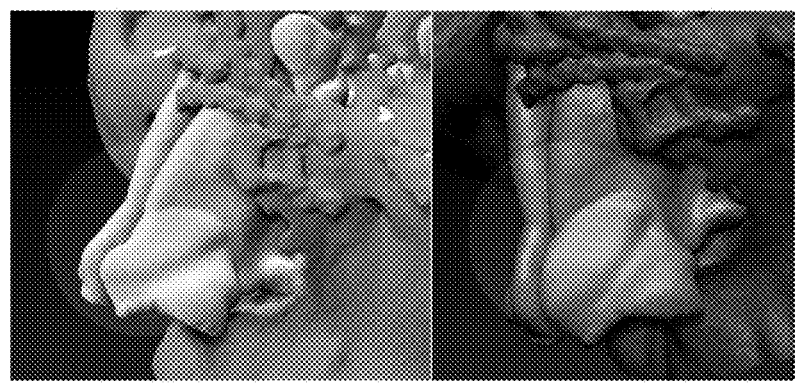
Figure 4:
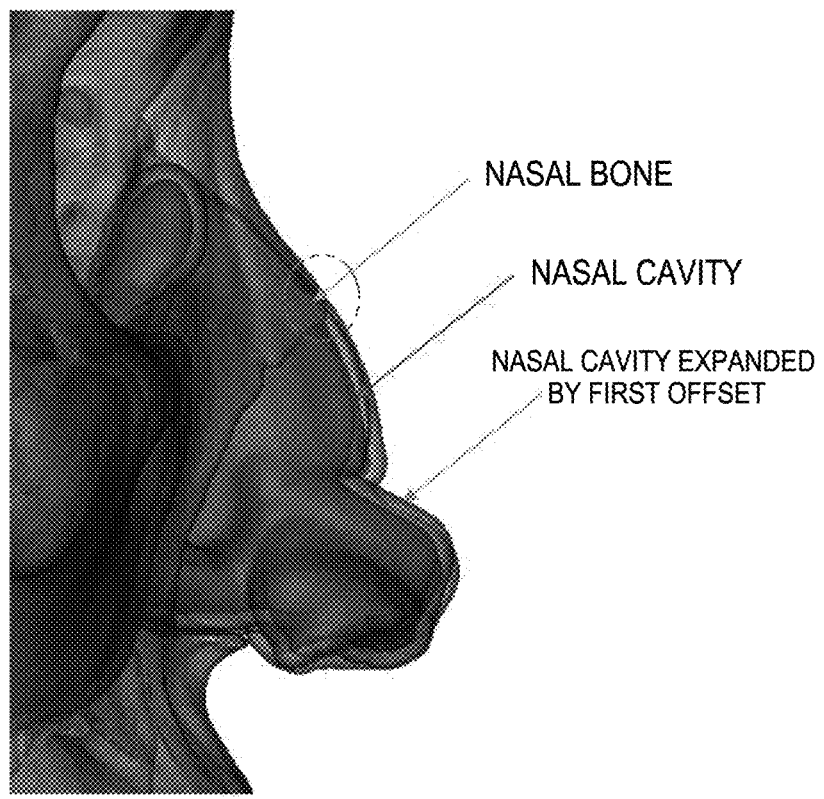
FIG. 4 is a view comparing whether the expanded nasal cavity has identical height of the nasal bone (the part in FIG. 4 indicated with a circle) from the 3-dimensional image of the nasal cavity expanded by applying an first offset and the 3-dimensional image of the nasal bone.
Figure 5C:
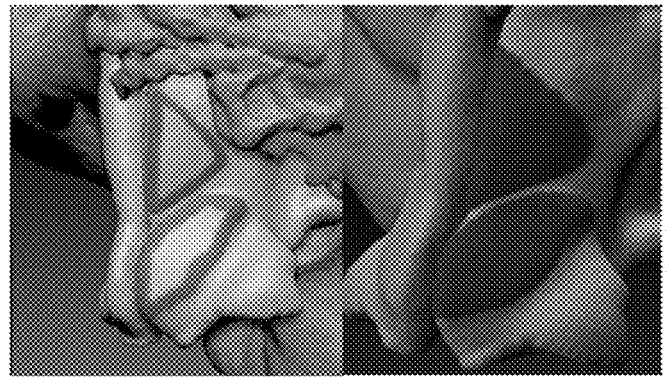
Figure 6A:
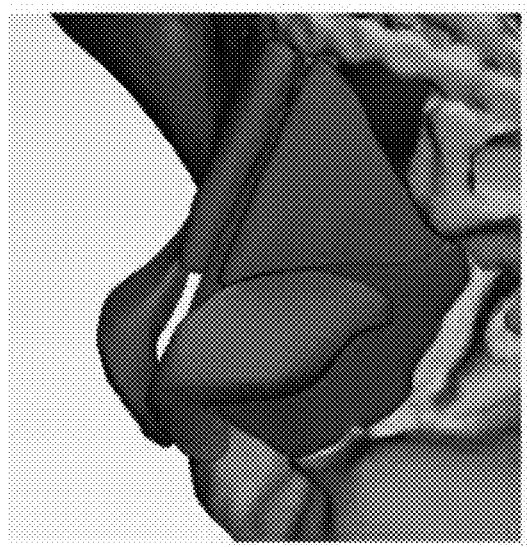
FIGS. 6(a) and 6(b) comparatively illustrate the lower lateral cartilage and the upper lateral cartilage modelled according to an embodiment of the present disclosure and a photograph of an actual nasal cartilage.
Figure 6B:
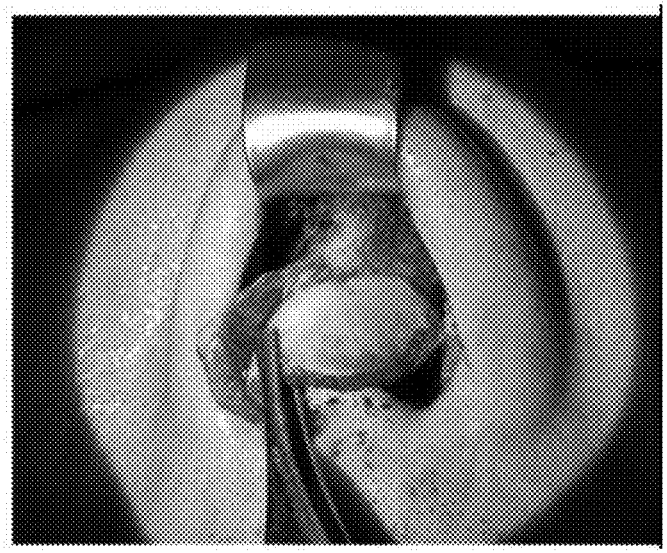
Figure 7A:
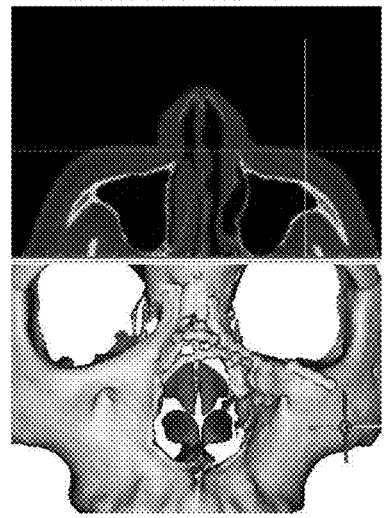
FIGS. 7(a)-7(c) illustrate a part of a process for modelling a septal nasal cartilage according to an embodiment of the present disclosure.
Figure 7B:
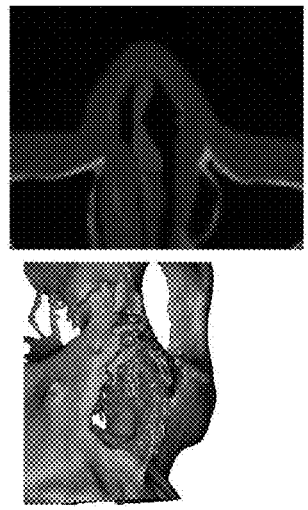
Figure 7C:
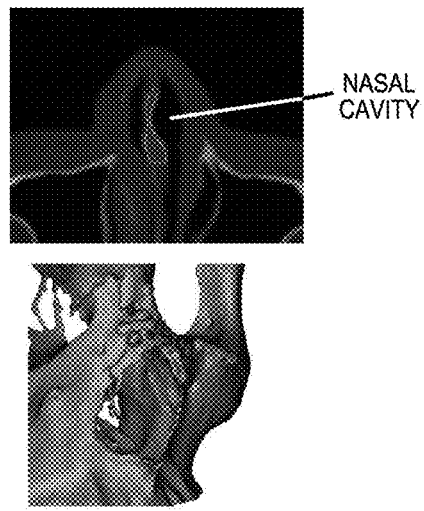
Figure 8:
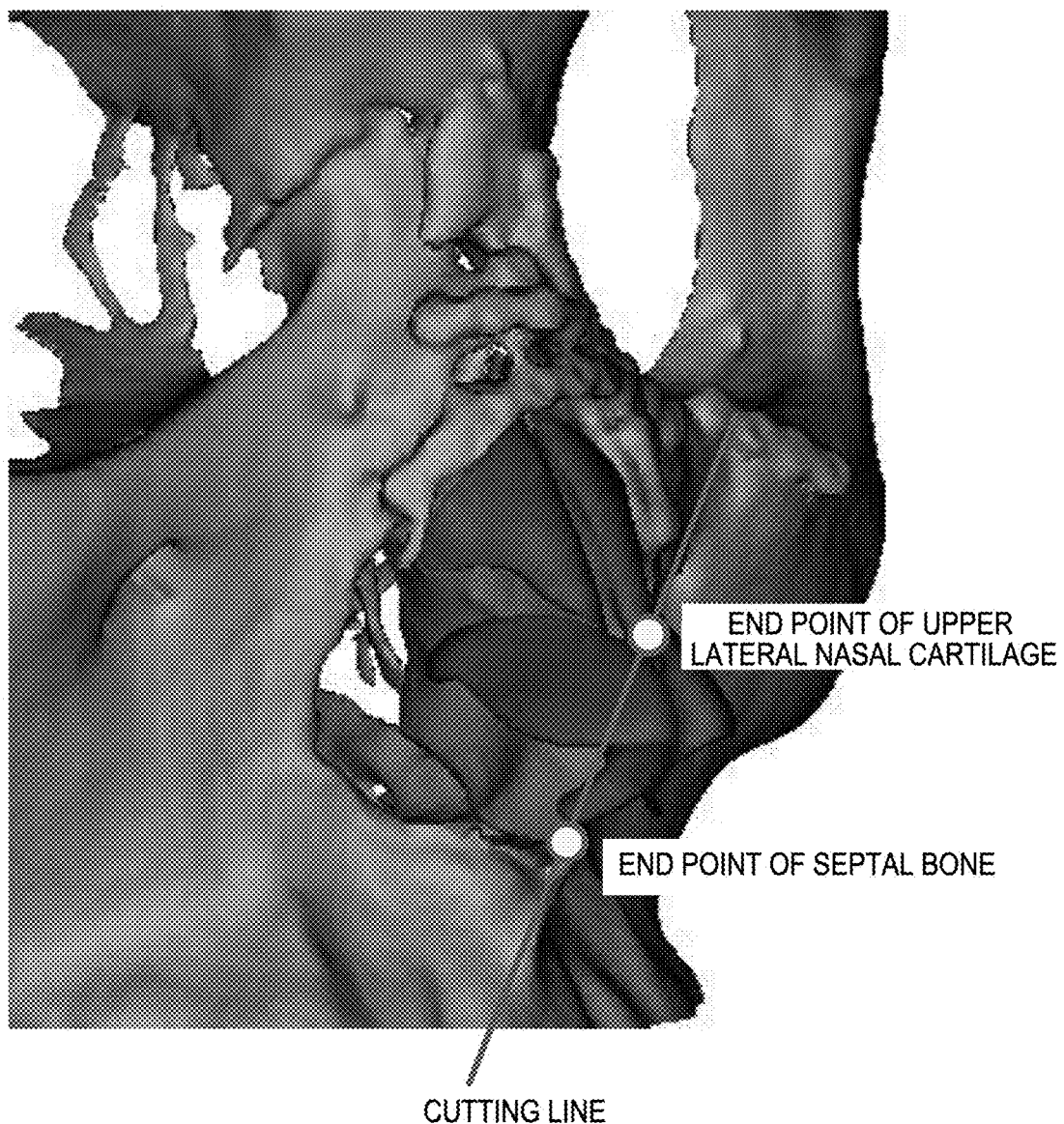
FIG. 8 illustrates a septal nasal cartilage finally modelled by modeling a ridge line of the spetal nasal cartilage after modeling both sides of the septal nasal cartilage according to FIG. 7, together with the modeled lover lateral cartilage and upper lateral cartilage.

FIGS. 3(a)-3(d) illustrate a part of a process for modelling a lower nasal cartilage and a upper lateral cartilage according to an embodiment of the present disclosure, FIG. 4 is a view comparing whether the expanded nasal cavity has identical height of the nasal bone from the 3-dimensional image of the nasal cavity expanded by applying an first offset and the 3-dimensional image of the nasal bone, FIGS. 5(a)-5(c) illustrate a part of the process for modelling the lower lateral cartilage and the upper lateral cartilage, following FIGS. 3(a)-3(d), FIGS. 6(a) and 6(b) comparatively illustrate the lower latera cartilage and the upper lateral cartilage modelled according to an embodiment of the present disclosure and a photograph of an actual nasal cartilage, FIGS. 7(a)-7(c) illustrate a part of a process for modelling a septal nasal cartilage according to an embodiment of the present disclosure, and FIG. 8 illustrates a septal nasal cartilage finally modelled by modeling a ridge line of the spetal nasal cartilage after modeling both sides of the septal nasal cartilage according to FIGS. 7(a)-7(c), together with the modeled lover lateral cartilage and upper lateral cartilage.

The nasal cartilage consists of a lower lateral cartilage or Alar cartilage, an upper lateral cartilage, and a septal nasal cartilage. First, a process for modelling the lower lateral cartilage and the upper lateral cartilage will be described.

In the present disclosure, the nasal cartilage is modelled using the 3-dimensional image of the nasal bone and the 3-dimensional image of the nasal cavity obtained by segmenting in the CT image. As in FIG. 3(a), if the image of the nasal cavity obtained from the CT image is not left-right symmetrical, it is possible to copy the image of the nasal cavity such that it is left-right symmetrical based on the nasal cavity having a form that is anatomically close to normal of the image of the left-right nasal cavity (FIG. 3(b)). In FIGS. 3(a)-3(d), the nasal cavity at the right (corresponding to the nasal cavity at the left side of the person receiving the treatment) has a shape that is close to normal anatomically, and therefore, the nasal cavity at the left side was made to be copied to be symmetrical to the right side.

Next, offset of an appropriate value is applied to the image FIG. 3(b) to expand the image of the nasal cavity, thereby expanding the size of the nasal cavity (FIG. 3(c)). Here, as illustrated in FIG. 4, with the 3-dimensional image of the nasal bone and the image of the nasal cavity expanded by applying offset placed to overlap each other, whether the expanded nasal cavity has identical height of the nasal bone is compared (the part in FIG. 4 indicated with a circle), and while adjusting the offset value such that the expanded nasal cavity has the identical height as the nasal bone (this may mean the expanded nasal cavity and the nasal bone being connected naturally without any step), an image of the expanded nasal cavity is obtained.

Anatomically, the nasal bone and the nasal cartilage have a naturally extending form, and the nasal cartilage has a thin film form having a predetermined thickness (about 0.5 mm), that is a form similar to the form of the edge of the nasal cavity. Therefore, the surface of the nasal cavity expanded by applying the offset may include a modelling shape of the outer side of the nasal cartilage.

Here, the offset value may have a value that is around 1.5 mm, which is a result obtained upon clinically identifying that when the image is expanded by applying the average offset of 1.5 mm to the image of the nasal cavity, the expanded cavity has an identical height as the nasal bone. Therefore, by adjusting the offset value based on 1.5 mm, it is possible to obtain an expanded image of the nasal cavity of the aforementioned condition. In the description below, the offset value being applied when expanding the image of the nasal cavity such that the height of the nasal bone and the nasal cavity are identical to each other will be referred to as a first offset.

Next, a second offset, obtained by subtracting a predetermined value corresponding to the thickness of the nasal cartilage from the first offset, may be applied to image FIG. 3(b), to obtain another expanded image of the nasal cavity (FIG. 3(d)). Here, the thickness of the nasal cartilage may be set to 0.5 mm, which is according to the average thickness of the clinically identified the lower lateral cartilage and the upper lateral cartilage. Therefore, the second offset may be a value obtained by subtracting 0.5 mm from the first offset. For example, when the value of the first offset is 1.5 mm, the value of the second offset may be 1 mm.

Therefore, FIG. 3(d) forms a standard surface of where a bottom surface of the nasal cartilage may be located, and the aforementioned FIG. 3(c) forms a standard surface of where a top surface of where the nasal cartilage may be located, thus the modelled nasal cartilage being placed between the two standard surfaces.

FIG. 5(a) illustrates an image showing the nasal cavity that has been expanded by applying the second offset as in FIG. 3(a), and in the present embodiment, the shape of the nasal cavity can be corrected according to the anatomical structure of the nasal cavity in the 3-dimensional image of the nasal cavity that has been expanded by applying the second offset (FIG. 5(b)). Here, any excessively dented or distorted portion compared to a generally known anatomical structure of the nasal cavity can be corrected to a smooth shape by connecting end points of non-distorted portions and giving natural volume.

Next, based on the area most prominently protruding from the surface of the 3-dimensional image from the corrected image, outlines of the lower lateral cartilage and the upper lateral cartilage are created (FIG. 5(c)).

Next, as aforementioned, according to the clinical average, the thickness of the cartilage is 0.5 mm, and thus it is possible to finally model the lower lateral cartilage and upper lateral cartilage by applying the thickness of 0.5 mm to the outlines.

FIGS. 6(a) and 6(b) compare the lower lateral cartilage and upper lateral cartilage modelled according to the present disclosure, with a photograph of an actual nasal cartilage, which shows that the lower lateral cartilage and upper lateral cartilage modelled according to the present disclosure have been modelled anatomically almost the same as the actual nasal cartilage.

In the present embodiment, the process for modelling the entirety of the lower lateral cartilage and upper lateral cartilage was described together with the drawings, but since the place where the actual nasal implant is to be seated is the upper surface of the lower lateral cartilage and upper lateral cartilage, it is possible to model only the upper surface of the nasal cartilage from the image where the first offset has been applied as in FIG. 4, and use it to model the inner shape of the nasal implant as will be described hereinbelow.

Hereinbelow, the process for modelling a septal nasal cartilage will be described.

Anatomically, most of the surface of the inner shape on which nasal implant may be seated is supported from the lower lateral cartilage and upper lateral cartilage, but in the present embodiment, in order to increase the accuracy of modelling the nasal implant, a process for modelling the septal nasal cartilage may be further included.

As illustrated in FIG. 7(a), from the CT image, it is made to display the lower lateral cartilage and upper lateral cartilage modelled as aforementioned, and then an area between the nasal cavity at both sides, where the septal cartilage may be placed, is selected (FIG. 7(b)). Next, both sides of the septal cartilage may be modelled by applying a third offset to an edge line of the nasal cavity at both sides. Here, the septal nasal cartilage has a thickness of 0.5-1 mm, in the aforementioned image, and thus the third offset may be set considering this. Both sides of the nasal cavity are modelled in the present embodiment reflecting the anatomical fact that the septal nasal cartilage located between the nasal cavity at both sides are almost identical to the edge lines of the nasal cavity at both sides that are adjacent to the septal nasal cartilage.

Next, as illustrated in FIG. 8, the upper part of a ridge line of the septal nasal cartilage is formed between the upper lateral cartilage at both sides to slightly protrude by a predetermined height, and the lower part of the ridge line of the septal nasal cartilage may be modelled by cutting along a line that connects the position of the lower end point of the modelled upper lateral cartilage and the end point of the septal bone. FIG. 8 illustrates the septal cartilage finally modelled in the aforementioned method together with the upper lateral cartilage and lower lateral cartilage modelled as aforementioned.

After the nasal cartilage is modelled in the aforementioned method, the inner shape of where the implant may be seated is modelled using the 3-dimensional image of the nasal bone and the shape of the modelled nasal cartilage.

Figure 9A:
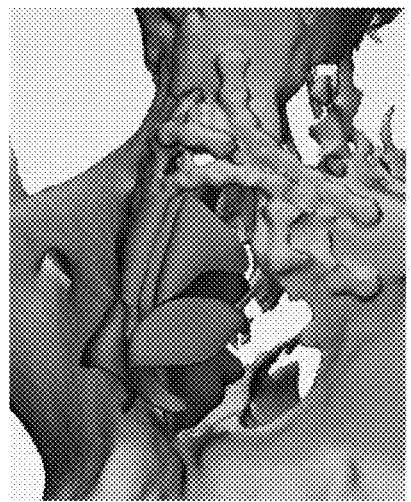
FIGS. 9(a)-9(c) illustrate a part of a process for modelling a standard shape of an inner shape where an implant may be seated using the cartilage modelled according to an embodiment of the present disclosure.
Figure 9B:
Figure 9C:
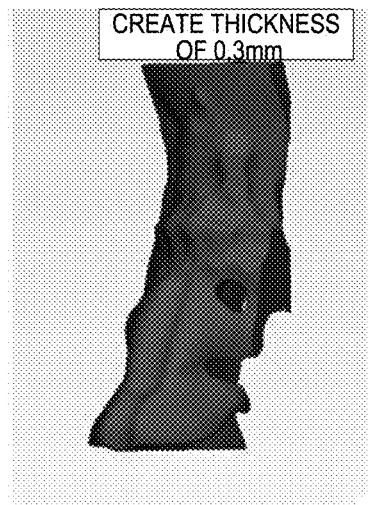
Figure 12A:
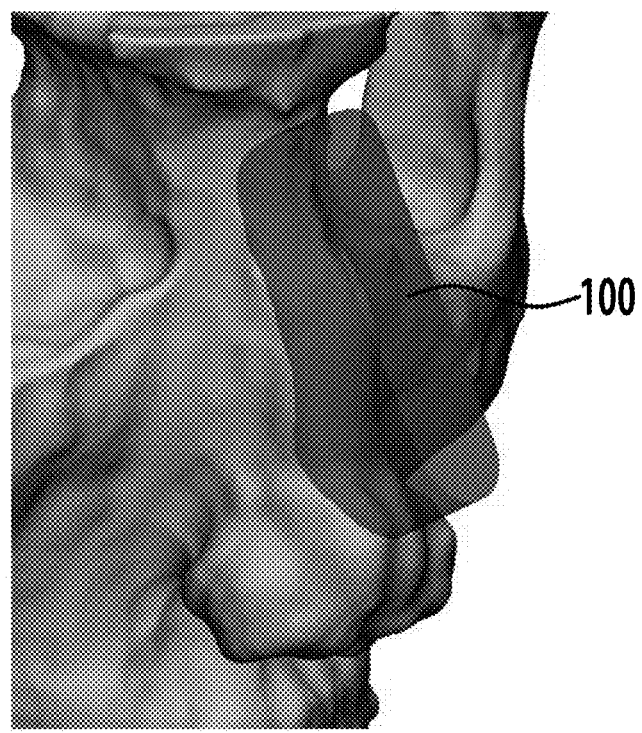
FIGS. 12(a) and 12(b) illustrate a process for modelling the inner shape of the implant according to the standard shape in FIG. 10.
Figure 10:
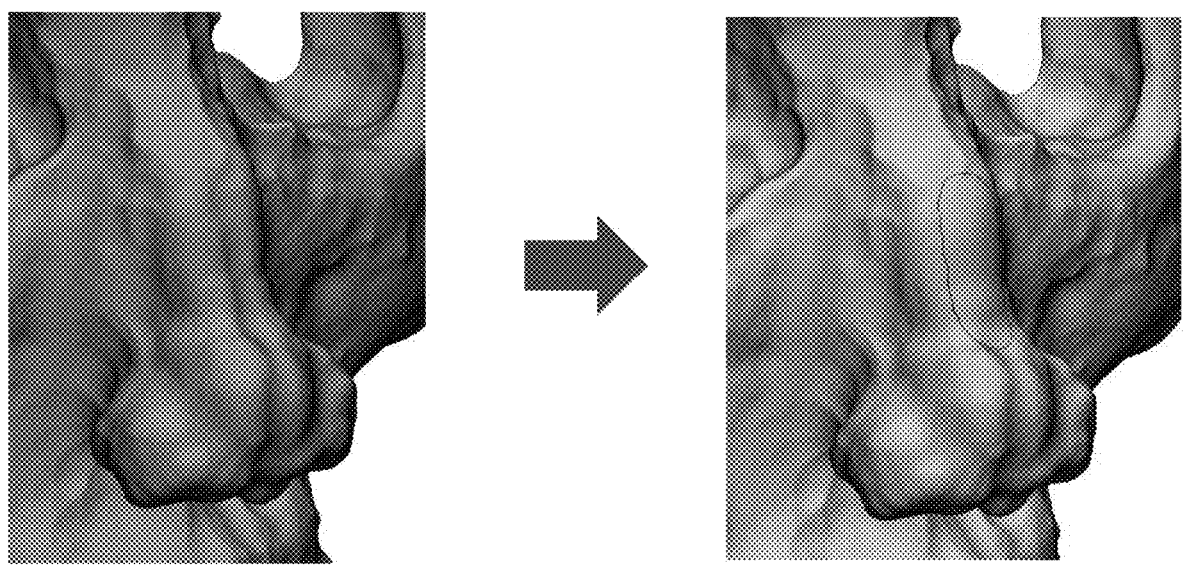
FIG. 10 illustrates before and after state of convexly correcting the concave portion between the upper lateral cartilages after modeling a mucous membrane.
Figure 11:
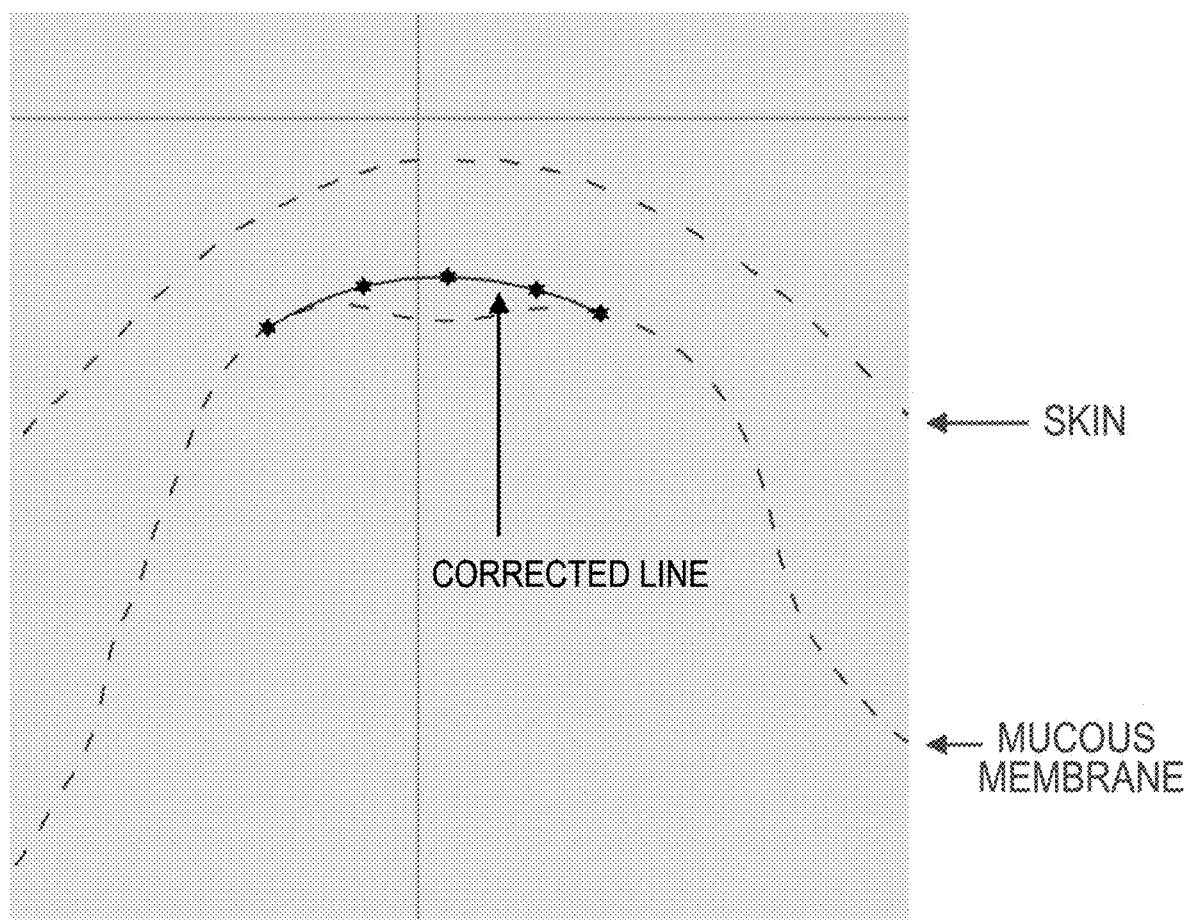
FIG. 11 is a view for describing the process of FIG. 10.
Figure 12B:
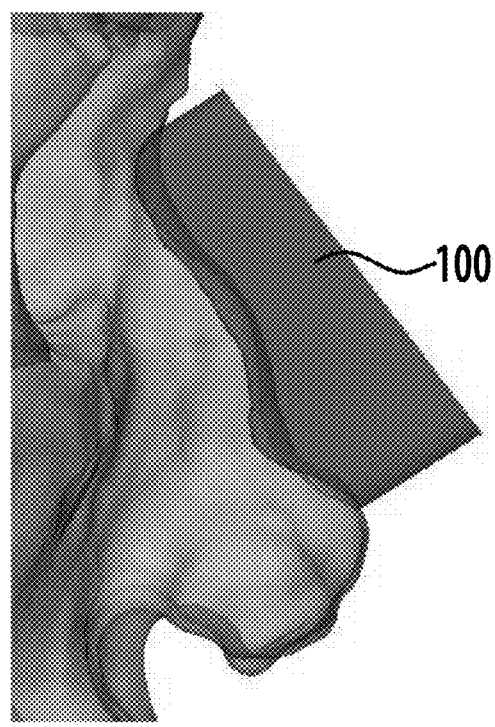
Figure 13:
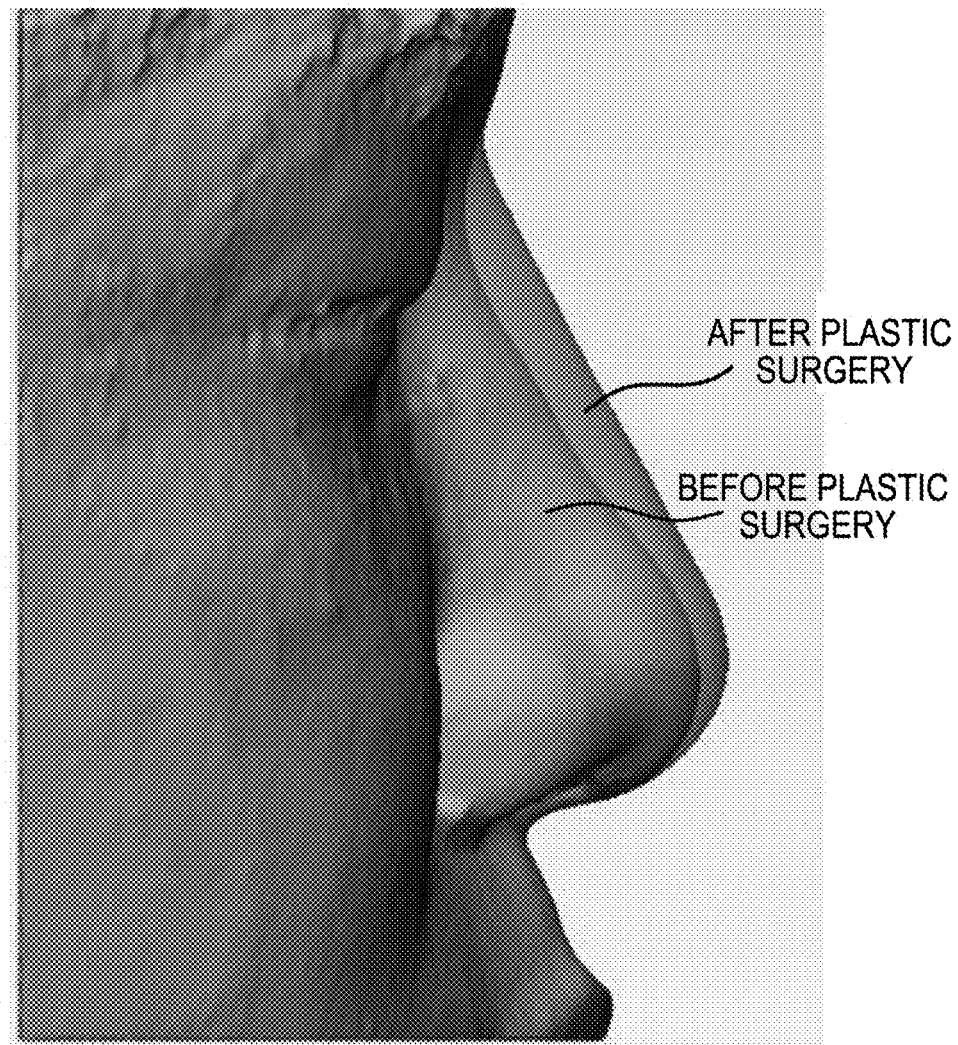
FIG. 13 is a view that illustrates a 3-dimensional appearance of a nose before a plastic surgery and a 3-dimensional appearance of the nose desired after the plastic surgery.
Figure 14:
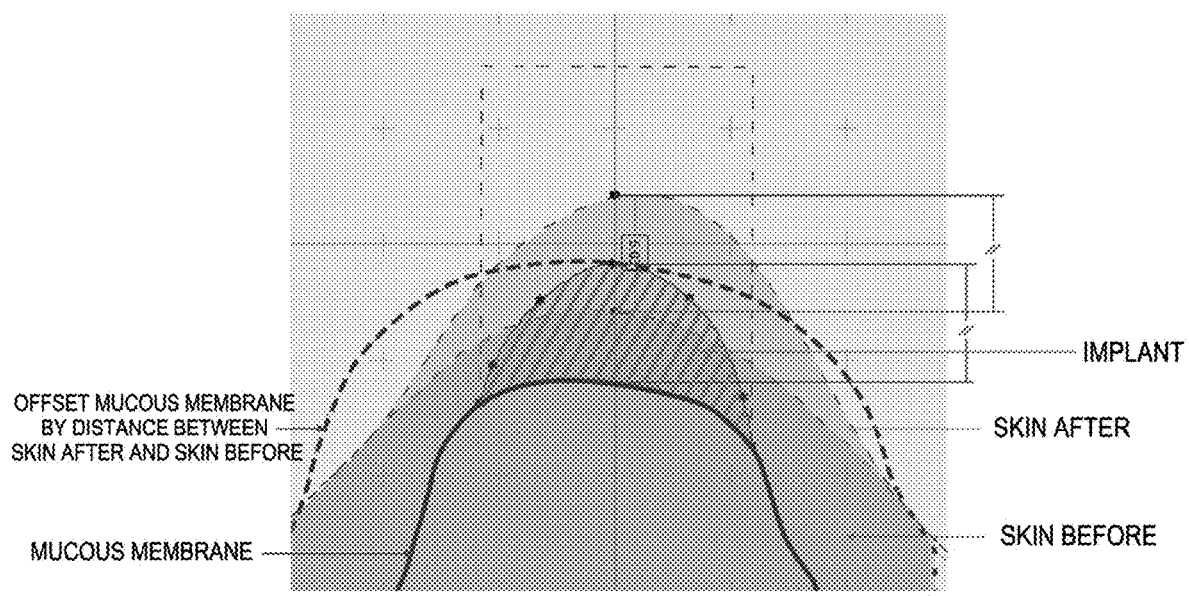
FIG. 14 is a view for describing a process for modelling an outer shape of a nose implant
Figure 15:
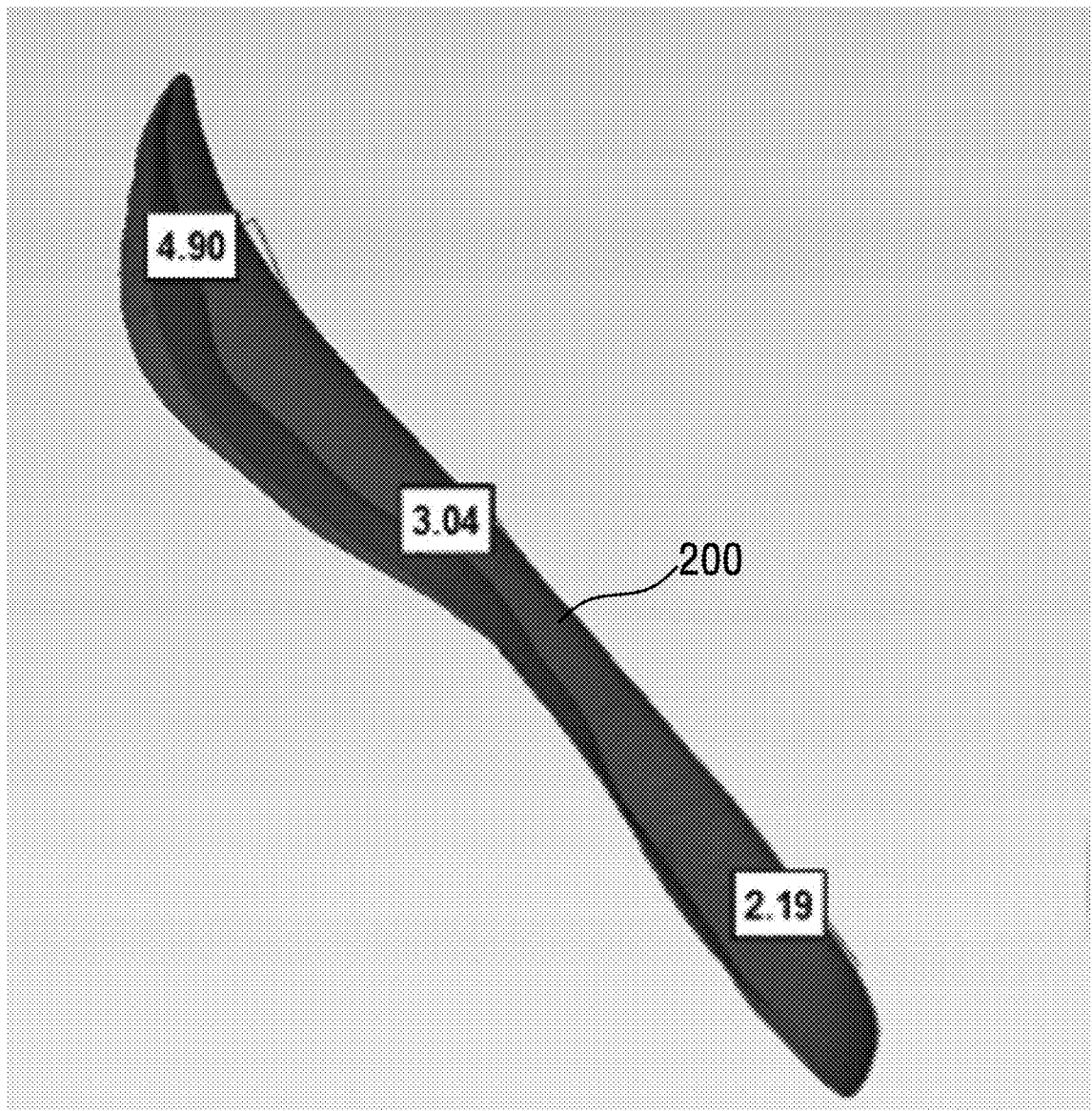
FIG. 15 is a view illustrating a finally modelled nose implant according to an embodiment of the present disclosure.

FIGS. 9(a)-9(c) illustrate a part of a process for modelling a standard shape of an inner shape where an implant may be seated using the cartilage modelled according to an embodiment of the present disclosure, FIG. 10 illustrates before and after state of convexly correcting the concave portion between the upper lateral cartilages after modeling a mucous membrane, FIG. 11 is a view for describing the process of FIG. 10, FIGS. 12(a) and 12(b) illustrate a process for modelling the inner shape of the implant according to the standard shape in FIG. 10, FIG. 13 is a view that illustrates a 3-dimensional appearance of a nose before a plastic surgery and a 3-dimensional appearance of the nose desired after the plastic surgery, FIG. 14 is a view for describing a process for modelling an outer shape of a nose implant, FIG. 15 is a view illustrating a finally modelled nose implant according to an embodiment of the present disclosure, and FIG. 16 is a view illustrating a mold modelled in order to manufacture the nose implant of FIG. 15.

First, as in FIG. 9(a), the 3-dimensional image of the nasal bone and the modelled cartilage are overlapped with each other, and in the method of merging by connecting the lines of the nasal bone and the cartilage, an inner line of the implant is created as in FIG. 9(b).

The image where the nasal cavity has been expanded by the first offset as aforementioned forms the upper surface of the lower lateral cartilage and upper lateral cartilage where the implant may be seated, and thus by connecting and merging the image expanded by the first offset and the image of the bone, the inner line of the implant may be created.

Next, in image FIG. 9(b), a fourth offset, which corresponds to the thickness of the mucous member, is applied so as to expand the image by a constant ratio in the same method as aforementioned (FIG. 9(c)). This is to take into consideration the mucous membrane having a predetermined thickness, formed on top of the nasal bone and cartilage. According to the clinical average, the thickness of the mucous membrane may be 0.3 mm.

Therefore, an image where the 3-dimensional image of the nasal bone and the modelled cartilage have been connected and merged, and then expanded by applying the fourth offset (FIG. 9(c)) may finally be the standard surface of the inner shape of the nasal implant.

Desirably, it is possible to correct the dented part between the upper lateral cartilages modelled as illustrated in FIGS. 10 to 11, to protrude convexly by naturally extending the line of the surrounding mucous membrane (upper lateral cartilage) as illustrated in FIG. 11.

Next, as illustrated in FIGS. 12(a) and 12(b), by creating an implant base 100 that extends from the root of the nose to the tip of the nose, and overlapping the standard surface of the inner shape of the implant finally modelled in consideration of the thickness of the mucous membrane, and then removing the overlapping part, it is possible to model the inner shape of the implant.

The outer shape of the implant is modelled after modelling the inner shape of the implant. The outer shape of the nasal implant determines the outer form of the nose after the plastic surgery, and may be designed by reflecting the requirements of the person being treated and the opinion of the person performing the treatment.

Here, based on the inner shape of the implant of which the inner shape has been modelled, a predetermined thickness (for example, thickness of about 4 mm) may be created, and it is possible to derive the form of the outer shape of the implant where the requirements of the person being treated and/or opinions of the person performing the treatment have been reflected and do the modelling. In this process, it is preferable to obtain the difference of volume between the nose prior to the surgery and the nose modelled in the form after the surgery, and design the outer shape of the implant such that the increased volume has a similar value as the volume of the implant.

According to one embodiment for modelling the outer shape of the nose implant, first, it is possible to model the 3-dimensional image before the surgery and the 3-dimensional image after the surgery where the requirements of the person receiving the treatment and/or the opinions of the person performing the treatment have been reflected as illustrated in FIG. 13, and have them overlap each other and display the same.

Next, with respect to each cross-section that is vertical to the longitudinal direction of the nose of the implant, an outline of the implant is modelled. FIG. 14 illustrates the skin prior to plastic surgery, the skin after plastic surgery, and a cross-section where the implant is seated on top of the mucous membrane, the inner shape of the implant having been modelled by the aforementioned method in order to deform the skin from the skin prior to plastic surgery to the skin after plastic surgery. The difference of height of the ridge of the nasal point between before the plastic surgery and after the plastic surgery may be obtained, and from that, the height of the implant corresponding to the ridge of the nasal point can be obtained. Next, in the method of free-curve modelling between the ridge of the nasal point of the implant obtained in the aforementioned method and the inner shape edge of the implant modelled in the aforementioned method based on the shape of the skin after plastic surgery, it is possible to model the outline of the nasal implant. By modelling the outline of each cross-section in the aforementioned method, and by smoothly extending the outlines of each cross-section, it is possible to finally model the outer shape of the nasal implant.

FIG. 15 illustrates an embodiment of the shape of the nasal implant finally modelled by the aforementioned method.

Figure 16A:
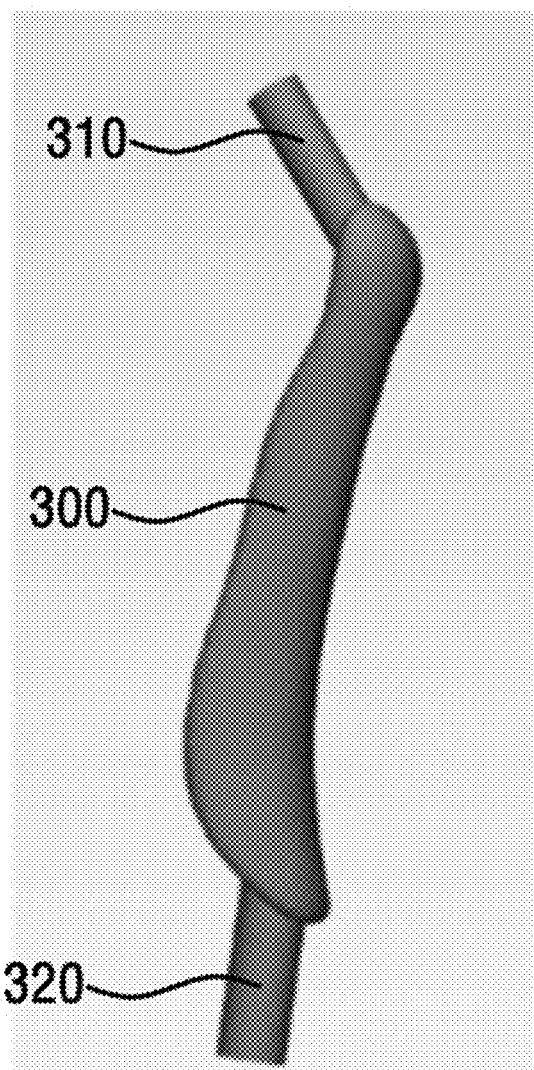
FIGS. 16(a) and 16(b) are views illustrating a mold modelled in order to manufacture the nose implant of FIG. 15.
Figure 16B:
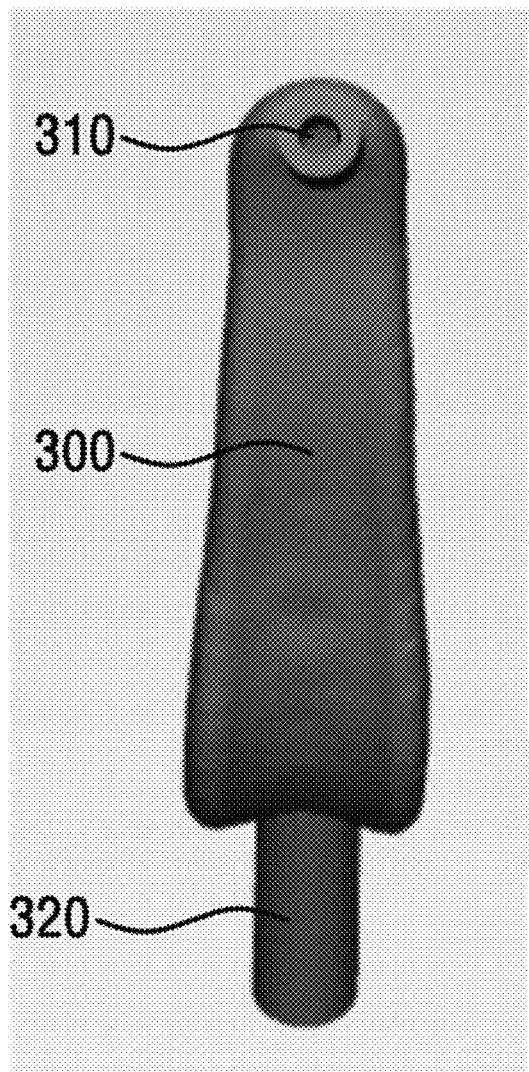

Next, a mold 300 for manufacturing a nasal implant in the form of the modelled nasal implant 200 is modelled as in FIGS. 16(a) and 16(b). On the above and below positions of the implant mold 300, an inlet 310 and outlet 320 for inject and discharging silicone for manufacturing the nasal implant, may be formed. The mold 300 that has been modelled as above may be manufactured using the 3D printer, but there is no limitation thereto.

Figure 17A:
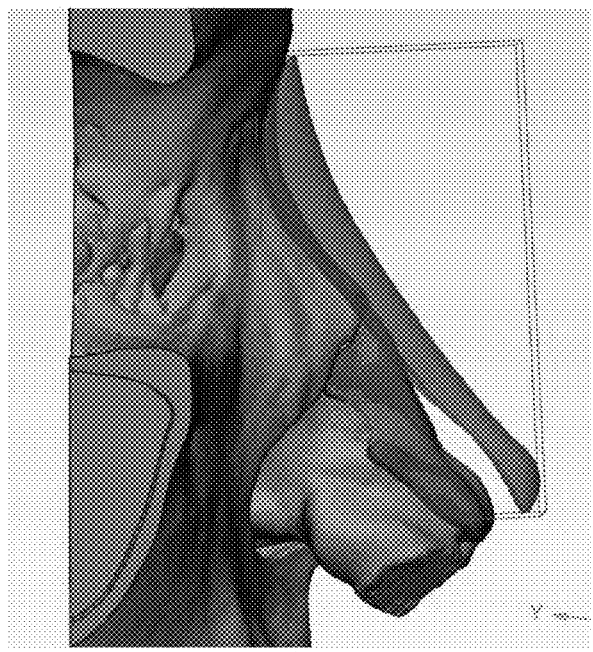
FIGS. 17(a) and 17(b) are views illustrating a conventional nose implant and a nose implant of the present disclosure seated on a nose.
Figure 17B:
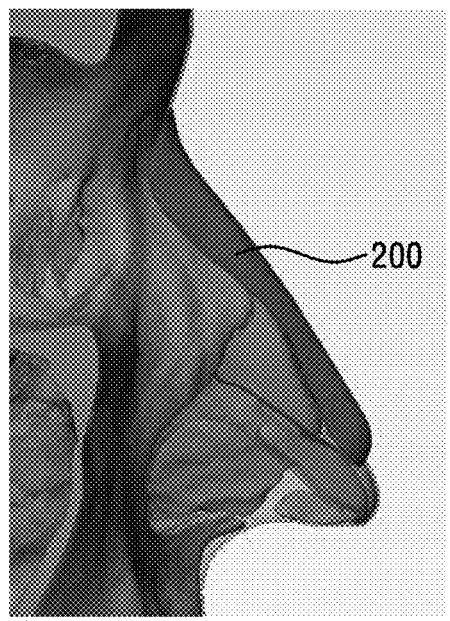

FIGS. 17(a) and 17(b) illustrate a conventional nose implant and a nose implant according to the present disclosure, each seated on the nose. FIG. 17(a) illustrates a nose implant selected from a conventional nose implant set, seated on the nose, and FIG. 17(b) illustrates a patient-customized nose implant manufactured according to the present disclosure, seated on the nose, wherein in the case of the conventional nose implant, the nose implant is not closely attached on top of the cartilage, and thus forms a space, whereas in the case of the present disclosure, the patient-customized nose implant can be closely attached on top of the cartilage, and thus it is possible to minimize side effects such as inflammation or position deformation and the like.

The scope of rights of the present disclosure is not limited to the embodiments described above, and the present disclosure can be implemented in various forms of embodiments within the claims set attached hereto. Without departing from the gist of the present disclosure claimed in the claims set, any person of ordinary skill in the art to which the present invention pertains is considered to be within the scope of the description of the claims of the present invention to various ranges that can be modified.

What is claimed is:

1. A method for manufacturing a nasal implant comprising:
   (a) obtaining a CT image, and segmenting a 3-dimensional image of a nasal bone from the CT image and segmenting a 3-dimensional image of a nasal cavity from the CT image;
   (b) modeling a nasal cartilage by applying information of anatomy between the nasal bone, the nasal cavity, and the nasal cartilage on to the 3-dimensional image of the nasal bone and the 3-dimensional image of the nasal cavity;
   (c) modeling an inner shape of the nasal cartilage of where the nasal implant is seated, from the 3-dimensional image of the nasal bone and the modelled nasal cartilage; and
   (d) manufacturing a mold based on the modelled nasal cartilage and manufacturing the nasal implant by providing silicon to the mold.

2. The method according to claim 1, wherein the CT image does not include identifiable nasal cartilage.

3. The method according to claim 1, wherein the step (b) comprises: repeatedly applying an offset to the 3-dimensional image of the nasal cavity and expanding the 3-dimensional image of the nasal cavity by a constant ratio; comparing the expanded 3-dimensional image of the nasal cavity and the 3-dimensional image of the nasal bone to determine whether the expanded nasal cavity is identical to a height of the nasal bone; and obtaining the expanded 3-dimensional image of the nasal cavity where a first offset has been applied, the first offset being the constant ratio enabling the expanded nasal cavity to be identical to the height of the nasal bone.

4. The method according to claim 3, further comprising, before the step (b), copying in the 3-dimensional image of the nasal cavity a left nasal cavity or a right nasal cavity based on a nasal cavity that is anatomically close to normal such that the 3-dimensional image of the naval cavity is symmetrical.

5. The method according to claim 3, further comprising:
   obtaining the 3-dimensional image of the nasal cavity, that has been expanded by the constant ratio, by applying a second offset obtained by subtracting a value corresponding to a thickness of the nasal cartilage from the first offset, in the 3-dimensional image of the nasal cavity;
   creating an outline of a lower lateral cartilage or Alar cartilage and an outline of an upper lateral cartilage on a surface of the 3-dimensional image of the nasal cavity, that has been expanded by applying the second offset; and
   modeling a 3-dimensional shape of the lower lateral cartilage or Alar cartilage and the upper lateral cartilage by applying the thickness of the nasal cartilage to the outline.

6. The method according to claim 5, further comprising, after the obtaining of the 3-dimensional image of the nasal cavity that has been expanded by the constant ratio by applying the second offset, correcting the shape of the nasal cavity according to anatomical structure in the 3-dimensional image of the nasal cavity, that has been expanded by applying the second offset.

7. The method according to claim 5, further comprising modeling both sides of a septal nasal cartilage by applying a third offset from the 3-dimensional image of the nasal cavity; and modeling a ridge line of the septa nasal cartilage according to a line connecting a location of an end point of the modelled upper lateral cartilage and an end point of a septal nasal bone, to model a 3-dimensional shape of the septal nasal cartilage.

8. The method according to claim 5, wherein the step (c) comprises;
   creating an inner shape line of the nasal implant by connecting a bone line in the 3-dimensional image of the nasal bone and a line of the modelled nasal cartilage;
   expanding the image where the bone line and the nasal cartilage line are connected by the constant ratio, by applying a fourth offset, that corresponds to a thickness of a mucous membrane; and modelling the inner shape of the nasal implant from the image expanded by the constant ratio by applying the fourth offset.

9. The method according to claim 1, wherein the step (d) comprises:

modeling an entirety of the nasal implant including modeling an outer shape of the nasal implant;

modelling the mold for manufacturing a shape of the modelled nasal implant;

manufacturing the mold; and manufacturing the nasal implant by injecting silicone into the mold.

10. The method according to claim 9, wherein the modelling of the outer shape of the nasal implant comprises:

regarding each cross-section vertical to a nasal longitudinal direction of the nasal implant, obtaining a height between the inner shape and the outer shape of the nasal implant from a difference of a height of a ridge of the nose point between skin before plastic surgery and skin after plastic surgery; and free-curve modelling between the ridge of the nose point of the nasal implant and an inner shape edge of the nasal implant, according to shape of the skin after plastic surgery.

11. The method according to claim 1, wherein the mold is manufactured using a 3D printer.

12. The method according to claim 7, wherein the step (c) comprises:

creating an inner shape hoe of the nasal implant by connecting a bone line in the 3-dimensional image of the nasal bone and a line of the modelled nasal cartilage;

expanding the image where the bone line and the nasal cartilage line are connected by the constant ratio, by applying a fourth offset, that corresponds to a thickness of a mucous membrane; and modelling the inner shape of the nasal implant from the image expanded by the constant ratio by applying the fourth offset.

* * * * *